United States Patent [19]

Tabacco et al.

[11] Patent Number: 4,507,388

[45] Date of Patent: Mar. 26, 1985

[54] UREA DETERMINATION METHOD

[75] Inventors: Alessandro Tabacco, Scanzorosciate; Franco Meiattini, Siena, both of Italy

[73] Assignee: Sclavo, Siena, Italy

[21] Appl. No.: 281,722

[22] Filed: Jul. 9, 1981

Related U.S. Application Data

[63] Continuation of Ser. No. 74,743, Sep. 12, 1979, abandoned.

[30] Foreign Application Priority Data

Sep. 15, 1978 [IT] Italy ............................... 27718 A/78

[51] Int. Cl.³ ................................................ C12Q 1/58
[52] U.S. Cl. ....................................................... 435/12
[58] Field of Search ............................................ 435/12

[56] References Cited

U.S. PATENT DOCUMENTS

| | | | |
|---|---|---|---|
| 3,119,751 | 1/1964 | Chaney | 435/12 |
| 3,432,395 | 3/1969 | Reardon | 435/12 |
| 3,542,649 | 11/1970 | Searcy | 435/12 |
| 3,592,741 | 7/1971 | Hughes | 435/12 |
| 3,769,172 | 10/1973 | Bressler et al. | 435/12 |
| 3,876,502 | 4/1975 | Monte et al. | 435/12 |

*Primary Examiner*—David M. Naff
*Assistant Examiner*—Randall E. Deck
*Attorney, Agent, or Firm*—Hedman, Gibson, Costigan & Hoare

[57] ABSTRACT

In a method for the enzymic-colorimetric determination of urea in clinical analyses, the improvement consisting in that the sample to be tested is admixed with a composite reagent composed by urease, a buffer, an alkali-metal salicylate and a nitroprusside and, after a short incubation, a hypochlorite is added, a short additional incubation is performed and the color is measured photometrically. By this method, two reagent systems are sufficient instead of the usual three.

8 Claims, No Drawings

UREA DETERMINATION METHOD

This is a continuation, of application Ser. No. 074,743 filed Sept. 12, 1979 now abandoned.

This invention relates to a simplified method for the enzymic-colorimetric determination of urea, which is based on the use of two reactive systems only.

It is known that the urease enzyme hydrolyses urea with attendant production of $CO_2$ and $NH_3$ (this being the enzymic portion of the determination (I).

It is also known that ammonia reacts with phenol and hypochlorite to form, in an alkaline environment, Indophenol Blue, which can be measured photometrically (this is the nonenzymic portion of the determination, known as the Berthelot reaction, Berthelot having described this reaction in 1859) (II, III, IV).

The sequence of the reactions to be exploited is indicated as follows:

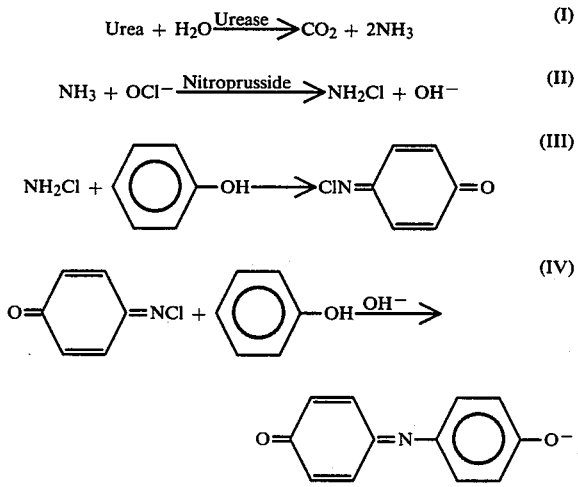

The sequence of the reactions II, III and IV has been studied and described by Weichselbaum et al (Anal. Chem. 41, 848, 1969) and recently by Patton et al (Anal. Chem., 49, 464, 1977).

In the reaction (II) the nitroprusside serves as a catalyst. It can be replaced by other substances, such as aquopentacyanoferrate.

Patton in his paper also described a few substituents for phenol to be used in the reactions III and IV. Among these, there is also the 2-carboxyl derivative, known also as the salicylic acid, Salicylic acid, or better the sodium salycylate, is used also in a few commercial kits for the dosage of urea (for example the Rochet kit).

However, all the papers and commercial kits known to the present applicants for the dosage of urea provide for three discrete reactive systems, viz.:
(a) Urease-buffer
(b) Phenol (or substituted phenol)-nitroprusside
(c) Alkali metal hypochlorite (or a substance having a like function).

Also the determination of urea is made in three stages, viz.:
(1) Admixing the sample with the Urease-buffer, and incubation
(2) Adding the phenol-nitroprusside
(3) Adding the hypochlorite, incubation and photometric readout.

The number of reagents and thus of the additions and steps cannot be reduced for the following reasons:

A. Phenol and/or hypochlorite cannot be admixed with urease since this enzyme is rapidly denaturated by these two substances.

B. Phenol and hypochlorite cannot be premixed together since the mixture rapidly loses its reactive ability, presumably due to the formation of chlorinated derivatives of phenol which are unsuitable for the reactive sequence aforementioned.

These long since deep-rooted ideas, have been regarded as valid hitherto also for substances which could replace phenol or the hypochlorite.

We have found that this is not true in a few cases. If, for example, salicylate is used instead of phenol, urease can be used simultaneously with it, and the sequence becomes as follows:

1. Admixing the sample with a reagent containing urease-buffer-salicylate (or an equivalent compound)-nitroprusside, and incubation.
2. Adding the hypochlorite, incubation and photometric readout.

As can be seen, the number of reagents passes from the three of the conventional systems, to two with the novel procedure. Likewise, the number of additions is diminished, that which brings about a considerable simplification, both when the urea determination is made manually (lesser number of pipetting steps) and when it is performed automatically (less intricate apparatus).

The novelty, thus, does not reside in the reaction sequence, as the reactions are, all of them, known and exploited long since, but in the fact that we have found that it is possible to admix and combine in a single reagent, urease, the buffer, the salicylate and the nitroprusside.

As outlined above, the salicylate can be replaced by a compound having an equivalent function and, among others, the use of the following substitutes has proven advisable: 3-methylsalicylic acid, 4-methylsalicylic acid and 3-hydroxybenzoic acid. It can be added, also, that the nitroprusside can be replaced, for example, by aquopentacyanoferrate. This result was actually unpredictable on the basis of the prior and contemporary arts.

The following example is reported by illustration only and must not be construed as a limitation.

EXAMPLE

The following solutions have been prepared:
(A) (with salicylate)
Components for 100 mls of solution:

| | |
|---|---|
| Phosphate buffer | 2 to 20 mols |
| Sodium salicylate | 0.4 to 4 g (grams) |
| Sodium nitroprusside | 50 to 500 mg (milligrams) |
| Urease | 2,000 to 20,000 Units |
| pH | 7.5 to 10.5 |

(B) (with 3-methyl salicylic acid)
Components for 100 mls of solution:

| | |
|---|---|
| $K_2HPO_4$ | 150 to 2,300 mg |
| 3-methyl salicylic acid | 30 to 300 mg |
| Sodium Nitroprusside | 30 to 500 mg |
| Urease | 2,000 to 20,000 Units |
| pH | 7.5 to 10.5 |

The reagents (A) and (B) reported above must be used in conjunction with the following reagent, (C), of which the concentration in readiness for use is reported hereunder:

| Sodium hypochlorite | 2 to 12 millimols |
|---|---|
| NaOH | 50 to 250 millimols |

2.5 mls of the reagent (A+B) and 0.020 mls of sample have been incubated for 5 to 10 minutes, whereafter 2.5 mls of the reagent (C) have been added thereto and the resultant solution has been incubate for 5 to 10 additional minutes.

The color which has been formed is measured at the spectrophotometer at 580 to 700 millimicrons.

We claim:

1. A method for the enzymic-colorimetric determination of urea comprising steps of:
    (a) admixing the sample to be tested with a reagent containing an admixture of urease, a phosphate buffer, a salicylate and an oxychlorination reaction catalyst selected from the group consisting of a nitroprusside and aquopentacyanoferrate.
    (b) incubating the admixture of step (a), and
    (c) adding a hypochlorite, and additionally incubating, and thereafter photometrically determining the amount of urea present.

2. A method according to claim 1, wherein the salicylate is replaced by 3-methyl-salicylic acid.

3. A method according to claim 1, wherein the salicylate is replaced by 4-methyl-salicylic acid.

4. A method according to claim 1, wherein the salicylate is replaced by 3-hydroxybenzoic acid.

5. A method according to claim 1, wherein the oxychlorination reaction catalyst is nitroprusside.

6. A method for the enzymic-colorimetric determination of urea which consists essentially of:
    (a) admixing the sample to be tested with a reagent containing an admixture of urease, a phosphate buffer, sodium salicylate, and an oxychlorination reaction catalyst selected from the group consisting of a nitroprusside and aquopentacyanoferrate;
    (b) incubating the product of step (a)
    (c) adding a hypochlorite,
    (d) incubating the product of step (c); and
    (e) photometrically determining the amount of urea that is present.

7. The method of claim 6, wherein the oxychlorination catalyst is sodium nitroprusside.

8. The method of claim 6, wherein the oxychlorination catalyst is aquopentacyanoferrate.

* * * * *